(12) United States Patent
Evans

(10) Patent No.: US 6,895,971 B1
(45) Date of Patent: May 24, 2005

(54) LIMB PROTECTION SYSTEM

(75) Inventor: Andrew James Evans, Pymble (AU)

(73) Assignee: Hydroskin Pty Ltd, Baulkham Hills (AU)

( * ) Notice: Subject to any disclaimer, the term of this patent is extended or adjusted under 35 U.S.C. 154(b) by 0 days.

(21) Appl. No.: 10/380,744

(22) PCT Filed: Sep. 21, 2000

(86) PCT No.: PCT/AU00/01153

§ 371 (c)(1),
(2), (4) Date: Jul. 10, 2003

(87) PCT Pub. No.: WO02/24014

PCT Pub. Date: Mar. 28, 2002

(51) Int. Cl.[7] ............................................. A61B 19/00
(52) U.S. Cl. ..................... 128/869; 128/878; 128/879; 128/882; 602/62
(58) Field of Search ................................. 128/869, 877, 128/878, 879, 880, 882, 846, DIG. 24; 602/61, 602/62, 63, 64, 65, 5; 2/16, 22

(56) References Cited

U.S. PATENT DOCUMENTS

| | | | |
|---|---|---|---|
| 3,872,515 A | 3/1975 | Boone et al. | |
| 4,180,065 A | 12/1979 | Bowen | |
| 4,346,699 A | 8/1982 | Little et al. | |
| 4,887,616 A * | 12/1989 | Baijnath | 128/879 |
| 4,901,372 A | 2/1990 | Pierce | |
| 4,966,135 A | 10/1990 | Renfrew | |
| 5,275,179 A * | 1/1994 | Lonardo | 128/882 |
| 5,407,421 A * | 4/1995 | Goldsmith | 602/5 |
| 5,592,953 A | 1/1997 | Delao | |
| 5,605,534 A | 2/1997 | Hutchison | |
| 5,678,248 A | 10/1997 | Lengyel | |
| 5,769,809 A * | 6/1998 | Witzel | 602/62 |
| 6,276,364 B1 * | 8/2001 | Warner | 128/846 |
| 6,726,641 B2 * | 4/2004 | Chiang et al. | 602/5 |

FOREIGN PATENT DOCUMENTS

| | | |
|---|---|---|
| DE | 8907170 | 9/1989 |
| EP | 0937447 | 8/1999 |
| FR | 2252839 A | 6/1975 |
| GB | 350851 | 6/1931 |
| GB | 2207337 | 2/1989 |
| GB | 2265314 A | 9/1993 |
| GB | 2287194 A | 9/1995 |
| NZ | 280249 A | 10/1997 |
| WO | WO 93/14730 A | 8/1993 |
| WO | WO 98/17340 A | 4/1998 |

* cited by examiner

*Primary Examiner*—Fadi H. Dahbour
(74) *Attorney, Agent, or Firm*—Timothy J. Keefer; Seyfarth Shaw LLP

(57) ABSTRACT

A limb protection device for protecting a section of a user's limb against contact comprises and enclosure for enclosing the limb section and at least one integral flexible cuff located at a respective limb entry to the enclosure. The cuff is adapted in use for being positioned against that part of the user's limb adjacent thereto to restrict the ingress of matter via the entry into the enclosure.

8 Claims, 3 Drawing Sheets

LIMB PROTECTION SYSTEM

FIELD OF THE INVENTION

The present invention relates to a limb protection system for protecting a section of a user's limb against moisture, gas, contact, bumping etc including against water and other fluids. The invention will be described primarily with reference to its use in medical/treatment applications, but it should be appreciated that the invention can be employed wherever it is necessary or desirable to protect a section of a user's limb against moisture, contact or the like. In addition, when the term "limb" is used herein, it is not simply intended to be limited to legs and arms of a user, but conceivably can extend to the torso etc of the user as appropriate, and not just human users, but animal users.

BACKGROUND ART

In medical treatment, it is often necessary/important to isolate a certain section of a limb from the remainder of the body of the animal (eg. human), to prevent it from contacting certain liquids (especially water), solvents, surfaces etc. For example, where the skin of a user's limb has been cut, grazed, burnt, bandaged, plastered etc., it is often necessary/desirable to prevent that area from being subjected to contact eg. with water or other liquids (or even gases).

Crude attempts at isolating such limb sections have been devised over time, the most common including the insertion of the limb section into a plastic bag, and then the positioning of an elastic or rubber band adjacent to the opening of the bag and extending around the perimeter of the limb. These crude systems are often inadequate in protecting the limb region from the ingress of moisture, gases etc. and are cumbersome to use.

Bag systems for positioning around the hand or feet of a user are shown in FR 2252839, GB 2265314, WO 98/17340, U.S. Pat. No. 4,966,135 and WO 93/14730. However, each of these documents disclose cumbersome or ineffective sealing mechanisms for preventing the ingress of unwanted matter into the bag (especially water). In particular, systems that are based around an adhesive attachment of the bag to the user's limb are disclosed in GB 2265314 and WO 98/17340. FR 2252839 discloses a separate elastic band securing system which may easily be dislodged, and is of a "primitive" nature in effect. U.S. Pat. No. 4,966,135, WO 93/14730 and NZ 280249 all disclose arrangements that only apply a line of force at an opening to a bag or cell which would rapidly become ineffectual over time or with repeated use.

SUMMARY OF INVENTION

The present invention provides a limb protection device for protecting a section of a user's limb, the device including:
   an enclosure for enclosing the limb section; and
   at least one flexible cuff integral with and away from which the enclosure extends, the cuff defining an opening into the device and being adapted for stretching around and compressing against that part of the user's limb extending therethrough in use, to prevent the ingress of matter into the device immediately at the device opening and for a width of cuff that is greater than a wall thickness of the enclosure.

In this way matter such as moisture (especially water) can be prevented from reaching the limb section. This is highly advantageous in many medical situations (eg. in bathing and showering of patients with wounds, bandages, plaster etc). Also, by defining a cuff in this manner a stronger, broader seal at the user's limb can be provided.

Preferably the cuff is formed from a different material, or a more dense form of the same material, as the enclosure. Typically the cuff is formed from a resilient polymeric material such as latex, elastic impregnated plastic, etc to enable its stretching during fitting and removal of the device to a limb.

Preferably the enclosure is a sleeve that is either:
   (a) closed at one end, with the cuff located at an opening at the other opposing end; or
   (b) open at opposing ends, with respective cuffs located at each end.

Arrangement (a) can be used for isolating entire feet, hands, legs or arms, whereas arrangement (b) can be used for isolating particular sections of limbs (eg. a forearm, wrist, shin, thigh) or for isolating joints (such as the elbow, shoulder, knee or hip).

In one alternative the sleeve in (a) can be releasably openable at said one end for enabling access to the limb section when, the device is fitted to a user (eg. for medical access, or to let air in, or for scratching, adjustments etc). In this regard, a press-seal opening can be employed at said one end.

Preferably the sleeve in (a) is adapted for receiving a user's hand or foot therein; and.

Preferably the sleeve in (b) is adapted for receiving the limb right therethrough with the cuff being located on opposing sides of the limb section that is enclosed within the enclosure.

Preferably the enclosure and/or the cuff are transparent. Preferably the enclosure is formed from a polymer that is integrally moulded with the cuff.

BRIEF DESCRIPTION OF THE DRAWINGS

Notwithstanding any other forms which may fall within the scope of the present invention, preferred forms of the invention will now be described, by way of example only, with reference to the accompanying drawings in which.

MODES FOR CARRYING OUT THE INVENTION

Figure 1:
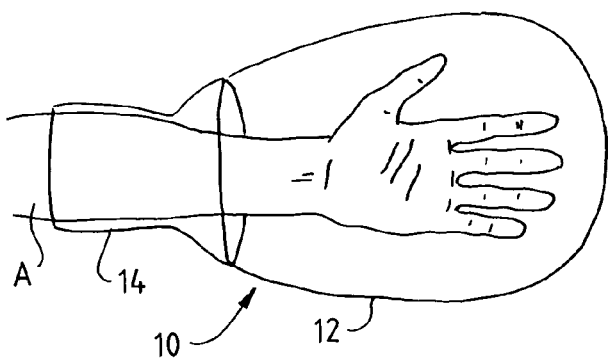
FIG. 1 shows a side elevation of a first limb protection device in use, in accordance with the present invention.
Figure 2:
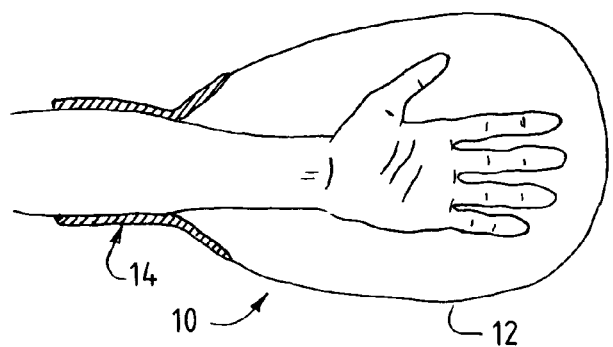
FIG. 2 shows the device of FIG. 1 in cross sectional side elevation.

Referring to the drawings, and in particular to FIG. 1, a limb protection device in the form of a protective bag 10 includes a sleeve portion 12 and an integral cuff portion 14. Typically both the sleeve portion and cuff portion are formed from thermoplastic polymers such that they can be moulded integrally together during original formation of the protective bag.

Typically the cuff portion is formed from a stretchable, resilient polymer, such as a latex or an elastic impregnated polymer to provide a close fit around the user's limb (eg. arm A). The bag at FIG. 1 is typically adapted for enclosing the hand/wrist of a user.

Typically the cuff portion has a diameter less than the arm of the user, so that it clasps peripherally around that limb when fitted. This provides a seal and, as can be seen, this seal can be provided over a relatively long area of limb, to maximise the sealing of the cuff against the ingress of matter (especially moisture). It has been observed that not only can the cuff seal against the ingress of any type of liquid, but it can also seal out gas, and lock air into the bag. Thus, the bag can also function like a balloon to protect the section of limb enclosed therein against inadvertent contact, bumping etc.

Typically the sleeve portion 12 is formed from a transparent polymer (such as polyethylene, polypropylene etc) to enable the user (and medical personnel) to maintain observation of the limb section enclosed therein.

Figure 3:
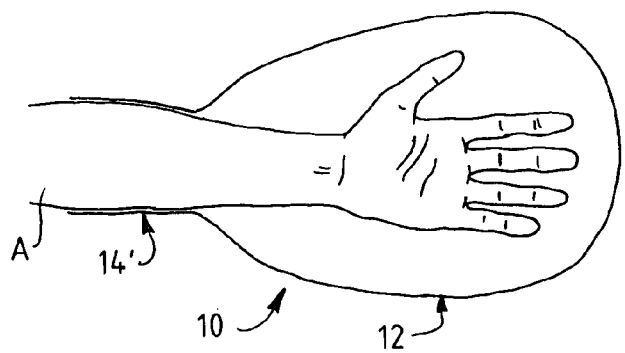
FIG. 3 shows in cross sectional side elevation an alternative device to that shown in FIGS. 1 and 2.

Referring now to FIG. 3, the cuff portion 14' can also be defined simply by a continuation of the sleeve portion 12 (ie. to be formed of the same material as the sleeve portion). Optionally, the cuff portion can have a thicker wall, or can be formed from a higher density version of the same material (eg. a low density polyethylene sleeve portion and a high density polyethylene cuff portion). Further, the cuff portion in FIG. 3 can be impregnated by an elastic material.

Figure 4:
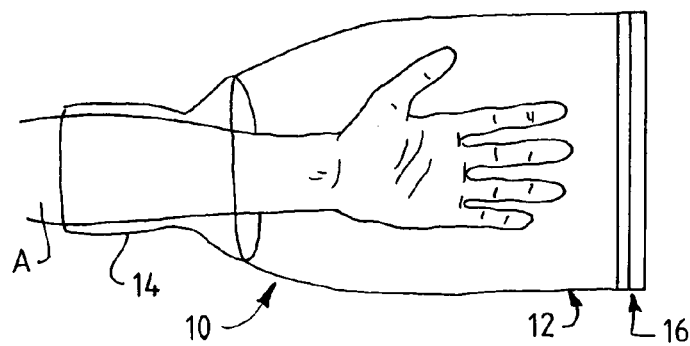
FIG. 4 shows a side elevation of a further alternative device to those shown in FIGS. 1–3.

Referring now to FIG. 4, the end of the bag opposing the cuff portion can be resealably openable, for example by having a press-seal opening 16 formed thereat. Other types of resealable openings can also be employed, such as those employing resealable waterproof contact adhesives etc.

Figure 5:
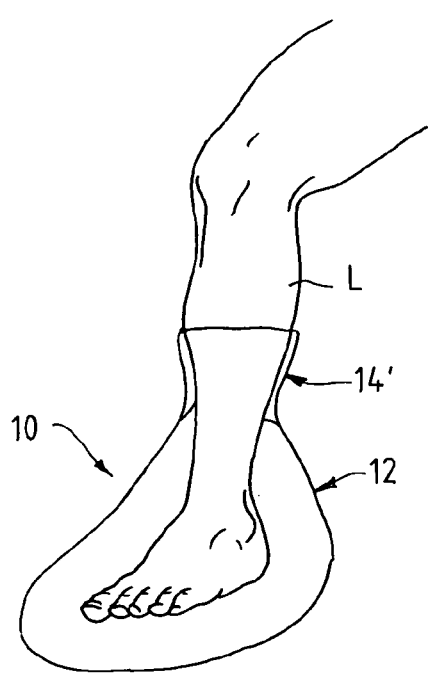
FIGS. 5 and 6 show, in side elevation, two further alternative limb protection devices for use with a foot/lower leg of a user.
Figure 6:
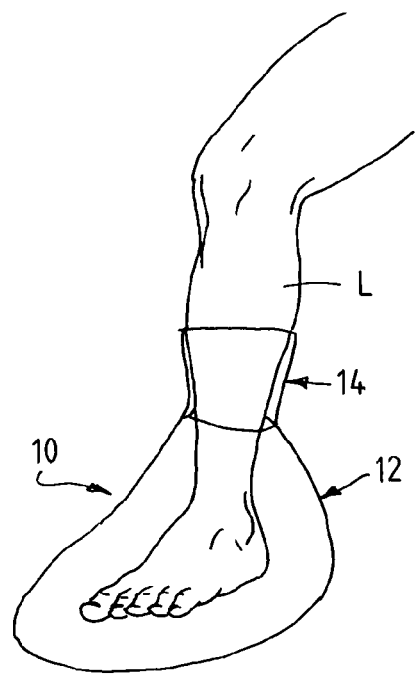

Referring now to FIGS. 5 and 6 where like reference numerals are used to denote similar or like parts, in this case the cuff portion 14, which in FIG. 5 is like that of FIG. 3 and in FIG. 6 is like that of FIG. 1, surrounds a shin and calf of the user to enclose the foot/ankle of the user. Either the same protective bag can be used for both the hand/wrist and the foot/ankle, or the bag can be a different size for foot/ankle usage.

Figure 7:
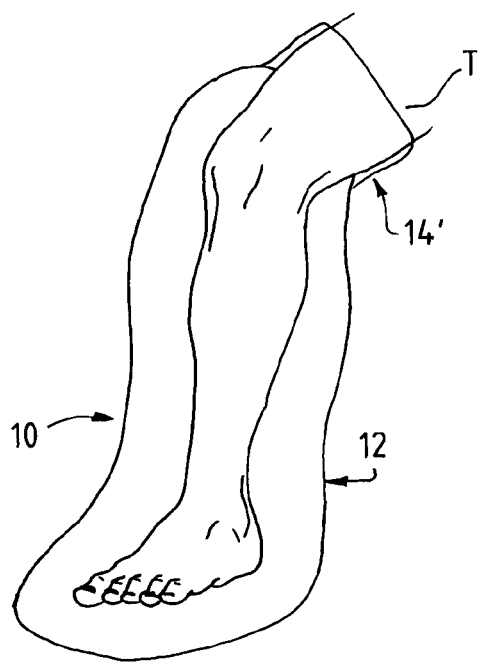
FIGS. 7 and 8 show, in side elevation, two further alternative devices for use with a user's leg.
Figure 8:
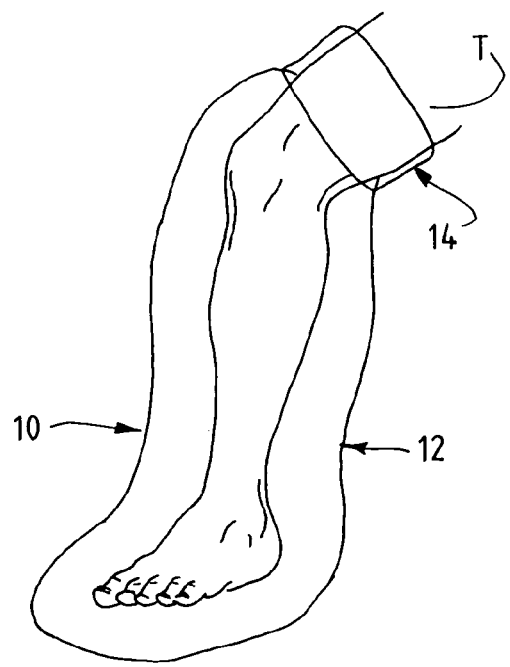

Referring now to FIGS. 7 and 8, again where like reference numerals are used to denote similar or like parts to that of FIGS. 5 and 6, in this case the sleeve portion 12 is substantially elongate, to fit both the foot, lower leg, knee, and lower thigh region of a user therein. In addition, the cuff portion is typically sized with a greater diameter to fit around the thigh T of a user.

Figure 9:
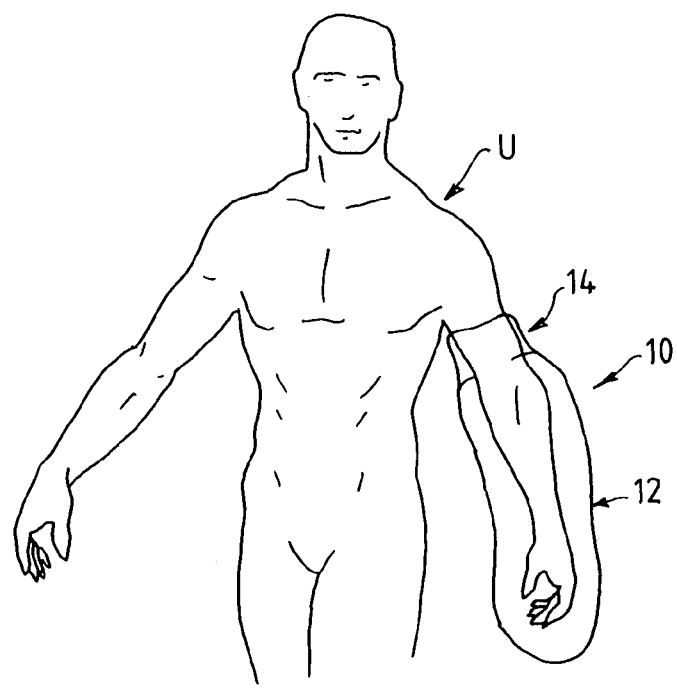
FIG. 9 shows, in side elevation, another limb protection device in accordance with the present invention.

Referring now to FIG. 9, where like reference numerals are used to denote similar or like parts, a differently shaped and elongated sleeve portion 12 is shown which is adapted for enclosing the hand and forearm of a user U.

Figure 10:
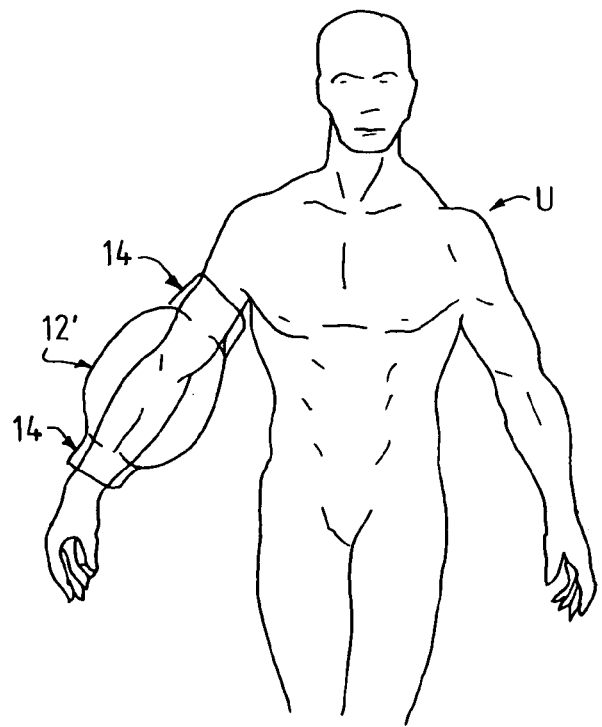
FIG. 10 shows in side elevation, yet a further limb protection device in accordance with the present invention.

Referring now to FIG. 10, where like reference numerals are used to denote similar or like parts, a further modified sleeve portion 12' includes a pair of opposing cuff portions 14. The upper cuff portion seals against the user's upper arm and the lower cuff portion seals against the forearm. The sleeve 12' thus isolates the user's elbow region, whilst still providing for hand and arm mobility A similar arrangement can be adapted for positioning around a user's knee region.

The embodiments described above most typically have medical applications, for protecting cuts, abrasions, burns, plasters, bandages etc against moisture, gas, contact, knocking and bumping. However, the arrangements can also be used in work and domestic applications wherever similar limb protection is required. The embodiments are particularly adapted for use by a user in showering and bathing applications.

Whilst the invention has been described with reference to a number of preferred embodiments, it should be appreciated that the invention can be embodied in many other forms.

What is claimed is:

1. A limb protection device for protecting a section of a user's limb including:
    an enclosure for enclosing the limb section; and
    at least one flexible cuff integral with and away from which the enclosure extends, the cuff defining an opening in the device and being adapted for stretching around and compressing against that part of the user's limb extending therethrough in use, to prevent the ingress of matter into the device immediately at the device opening and for a width of cuff that is greater than a wall thickness of the enclosure;
    wherein the enclosure is formed from a polymer that is integrally moulded with the cuff.

2. A device as claimed in claim 1, wherein the cuff is formed from a different material, or a more dense form of the same material, as the enclosure.

3. A device as claimed in claim 2, wherein the cuff is formed from a resilient polymeric material such as latex, or elastic impregnated plastic, to enable its stretching during fitting and removal of the device to a limb.

4. A device as claimed in claim 1, wherein the enclosure is a sleeve that is either:
    (a) closed at one end with the cuff located at an opening at the outer opposing end; or
    (b) open at opposing ends, with respective cuffs located at each end.

5. A device as claimed in claim 4, wherein the sleeve in (a) is releasably openable at said one end for enabling access to the limb section when the device is fitted to a user.

6. A device as claimed in claims 5, wherein a press-seal opening is provided at said one end.

7. A device as claimed in claim 4, wherein the sleeve in (a) is adapted for receiving a user's hand or foot therein, and the sleeve in (b) is adapted for receiving the limb right therethrough, with the cuff being located on opposing sides of the limb section that is enclosed within the enclosure.

8. A device as claimed in claim 1, wherein the enclosure and/or the cuff are transparent.

* * * * *